United States Patent [19]

Ieno et al.

[11] Patent Number: 5,424,437
[45] Date of Patent: Jun. 13, 1995

[54] PROCESS FOR PREPARING A 2-CHLORO-5-AMINOMETHYL-PYRIDINE

[75] Inventors: Katsuhiro Ieno; Yoshihiro Kawanami, both of Osaka, Japan

[73] Assignee: Koei Chemical Co., Ltd., Osaka, Japan

[21] Appl. No.: 188,705

[22] Filed: Jan. 31, 1994

[30] Foreign Application Priority Data

Feb. 1, 1993 [JP] Japan ................... 5-037518

[51] Int. Cl.$^6$ .................................. C07D 213/74
[52] U.S. Cl. ..................... 546/329; 546/332
[58] Field of Search ............. 546/250, 329, 332

[56] References Cited

U.S. PATENT DOCUMENTS 5,175,301 12/1992 Minamida et al. ................ 546/272

FOREIGN PATENT DOCUMENTS 0302389 2/1989 European Pat. Off. ............ 546/272
0512436 11/1992 European Pat. Off. ............ 546/272

Primary Examiner—C. Warren Ivy
Assistant Examiner—Zinna N. Davis
Attorney, Agent, or Firm—Wenderoth, Lind & Ponack

[57] ABSTRACT

A 2-Chloro-5-aminomethylpyridine is prepared in one step by reacting 2-chloro-5-trichloromethylpyridine with an amine and hydrogen in the presence of a hydrogenation catalyst.

7 Claims, No Drawings

PROCESS FOR PREPARING A 2-CHLORO-5-AMINOMETHYL-PYRIDINE

BACKGROUND OF THE INVENTION

1. Field of the Invention

The present invention relates to a novel process for preparing a 2-chloro-5-aminomethylpyridine. In particular, the present invention relates to a novel process for preparing a 2-chloro-5-aminomethylpyridine by reacting 2-chloro-5-trichloromethylpyridine, an amine and hydrogen in the presence of a hydrogenation catalyst.

A 2-Chloro-5-aminomethylpyridine is useful as intermediates in the synthesis of pharmaceuticals and agricultural chemicals.

2. Description of the Related Art

Hitherto, as a preparation process of a 2-chloro-5-aminomethylpyridine, there is known a process comprising reacting 2-chloro-5-monochloromethylpyridine and an amine (cf. Japanese Patent KOKAI Publication No. 171/1990).

However, the raw material 2-chloro-5-monochloromethylpyridine to be used in the above process is prepared by aminating 3-methylpyridine with a soda amide under high pressure to obtain 2-amino-5-methylpyridine and diazo decomposing and chlorinating it to obtain 2-chloro-5-methylpyridine and then chlorinating it. When 2-chloro-5-monochloromethylpyridine is prepared from 3-methylpyridine which is easily available commercially as this conventional preparation process, a number of process steps are required. In addition, 2-chloro-5-monochloromethylpyridine causes severe skin irritation. Therefore, the conventional process is not necessarily advantageous as the industrial production process.

SUMMARY OF THE INVENTION

An object of the present invention is to provide a novel process for the preparation of a 2-chloro-5-aminomethylpyridine, which has none of the above disadvantages of the conventional process.

Another object of the present invention is to provide a one step process for preparing a 2-chloro-5-aminomethylpyridine from 2-chloro-5-trichloromethylpyridine.

According to the present invention, there is provided a process for preparing a 2-chloro-5-aminomethylpyridine of the formula:

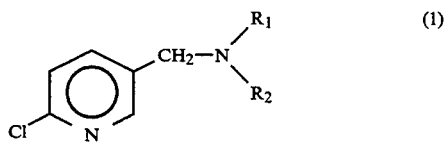
(1)

wherein $R_1$ is a hydrogen atom, an alkyl group or an aminoalkyl group, and $R_2$ is a hydrogen atom or an alkyl group, comprising reacting 2-chloro-5-trichloromethylpyridine with an amine of the formula:

(2)

wherein $R_1$ and $R_2$ are the same as defined above and hydrogen in the presence of a hydrogenation catalyst.

In the formulas (1) and (2), the alkyl group for $R_1$ and $R_2$ and in the aminoalkyl group is an alkyl group having 1 to 8 carbon atoms. Examples of the alkyl group are a methyl group, an ethyl group, a propyl group, a butyl group and the like. Examples of the aminoalkyl group for $R_1$ are a 2-aminoethyl group, a 2-aminopropyl group, a 3-aminopropyl group, a 2-aminobutyl group, a 3-aminobutyl group, a 4-aminobutyl group, and the like.

Examples of the amine (2) are ammonia, monoalkylamines (e.g. methylamine, ethylamine, etc.), diamines (e.g. ethylenediamine, 1,2-diaminopropane, 1,4-diaminobutane, etc.), dialkylamines (e.g. dimethylamine, diethylamine, etc.) and the like. These amines may have a protective group to prevent the formation of a by-product. An amount of the amine (2) is usually from 1 to 20 moles, preferably from 2 to 10 moles per one mole of 2-chloro-5-trichloromethylpyridne.

In the process of the present invention, hydrogen chloride is formed as a by-product by the reaction of liberated chlorine atom and hydrogen. While it is possible to neutralize hydrogen chloride with an excessive amount of the amine (2), it may be possible to add a tertiary amine to the reaction system for neutralizing hydrogen chloride.

Preferred examples of the 2-chloro-5-aminomethylpyridine (1) are 2-chloro-5-aminomethylpyridine, 2-chloro-5-methylaminomethylpyridine, 2-chloro-5-ethylaminomethylpyridine, 2-chloro-5-(2-aminoethyl)aminomethylpyridine, 2-chloro-5-(2-aminopropyl)aminomethylpyridine, 2-chloro-5-dimethylaminomethylpyridine, 2-chloro-5-diethylaminomethylpyridine, and the like.

Preferred examples of the hydrogenation catalyst are Raney catalysts (e.g. Raney nickel, Raney cobalt, etc.), noble metal catalysts (e.g. ruthenium/carbon, rhodium/carbon, platinum/carbon, etc.), and the like. Among them, Raney nickel is particularly preferred.

When Raney nickel is used as the hydrogenation catalyst, reduction of the chloro substituent at the 2-position on the pyridine nucleus, namely dechlorination, hardly proceeds, so that only the trichloromethyl group on the side chain is dechlorinated.

An amount of the hydrogenation catalyst is 1 to 50% by weight, preferably from 5 to 20% by weight based on the weight of 2-chloro-5-trichloromethylpyridine.

In the process of the present invention, a solvent may be used. Examples of the solvent are an alcohol (e.g. methanol, ethanol, isopropanol, etc.), a polar solvent (e.g. water), a non-polar solvent (e.g. benzene, toluene, xylene, etc.), and the like. An amount of the solvent is 0 to 20 parts by weight, preferably from 0 to 3 parts by weight per one part by weight of 2-chloro-5-trichloromethylpyridine.

A pressure of hydrogen to be reacted is from an atmospheric pressure to 100 Kg/cm², preferably from an atmospheric pressure to 30 Kg/cm². A reaction temperature is from 0° to 100° C., preferably from 10° to 50° C.

In one of preferred embodiments of the present invention, the amine (2) and the hydrogenation catalyst are charged in a reactor, and then the reaction is carried out while supplying hydrogen and 2-chloro-5-trichloromethylpyridine. After the supply of 2-chloro-5-trichloromethylpyridine is finished, hydrogen is further supplied till no further hydrogen is absorbed to complete the reaction. During the supply of 2-chloro-5-trichloromethylpyridine, the reaction temperature is preferably not more than 40° C.

By the above preferred embodiment, decomposition of 2-chloro-5-trichloromethylpyridine is suppressed, and the 2-chloro-5-aminomethylpyridine (1) can be safely prepared at a high yield.

The 2-chloro-5-aminomethylpyridine (1) may be isolated and purified by a per se conventional manner. For example, after the completion of reaction, the hydrogenation catalyst is removed from the reaction mixture by filtration, the reaction mixture is neutralized, and the solvent is evaporated off. Thereafter, water is added to the residue and then the poroduct is extracted with toluene. After phase separation, the toluene layer is concentrated and distilled.

PREFERRED EMBODIMENTS OF THE INVENTION

The present invention will be illustrated by the following Examples, which do not limit the present invention in any way.

Example 1

In a 120 cc autoclave equipped with a magnetic stirrer, 2-chloro-5-trichloromethylpyridine (11.5 g), Raney nickel (1.15 g) and a 70% aqueous solution of ethylamine (32.2 g) were charged. Hydrogen gas was introduced into the autoclave to a pressure of 10 Kg/cm$^2$, and an internal temperature was raised to 45° C. At the same temperature, the hydrogen gas was supplied under a hydrogen pressure of 5 to 12.5 Kg/cm$^2$. The absorption of hydrogen ceased after 70 minutes from the start of hydrogen supply. After completion of reaction, the autoclave was cooled to room temperature, and the catalyst was filtrated off from the reaction mixture. The filtrate was adjusted to pH 12.9 with a 48% aqueous solution of sodium hydroxide and the filtrate was concentrated. Water was added to the concentrate, and the product was extracted with toluene twice. After phase separation, the toluene layer was concentrated to obtain a concentrate (8.0 g) containing 2-chloro-5-ethylaminomethylpyridine, which was analyzed by gas chromatography to find that a yield of 2-chloro-5-ethylaminomethylpyridine was 77%.

Example 2

In a 119.5 cc autoclave equipped with a magnetic stirrer, 2-chloro-5-trichloromethylpyridine (11.5 g), ethanol (20 g), Raney nickel (1.15 g) and a 40% aqueous solution of methylamine (27.2 g) were charged. Hydrogen gas was introduced into the autoclave to a pressure of 10 Kg/cm$^2$, and an internal temperature was raised to 45° C. At the same temperature, the hydrogen gas was supplied under a hydrogen pressure of 7 to 13 Kg/cm$^2$. The absorption of hydrogen ceased after 95 minutes from the start of hydrogen supply. After completion of reaction, the autoclave was cooled down to room temperature, and the catalyst was filtrated off from the reaction mixture. The filtrate was adjusted to pH 12.9 with a 48% aqueous solution of sodium hydroxide and the filtrate was concentrated. Water was added to concentrate, and the product was extracted with toluene twice. After phase separation, the toluene layer was concentrated to obtain a concentrate (4.9 g) containing 2-chloro-5-methylaminomethylpyridine, which was analyzed by gas chromatography to find that a yield of 2-chloro-5-methylaminomethylpyridine was 45%.

Example 3

In a 119.5 cc autoclave equipped with a magnetic stirrer, 2-chloro-5-trichloromethylpyridine (11.5 g), Raney nickel (1.15 g), ethylenediamine (21.0 g) and ethanol (20 g) were charged. Hydrogen gas was introduced into the autoclave to a pressure of 10 Kg/cm$^2$, and an internal temperature was raised to 45° C. At the same temperature, the hydrogen gas was supplied under a hydrogen pressure of 7 to 11.2 Kg/cm$^2$. The absorption of hydrogen ceased after 180 minutes from the start of hydrogen supply. After completion of reaction, the autoclave was cooled down to room temperature, and the catalyst was filtrated off from the reaction mixture. The filtrate was adjusted to pH 13.7 with a 48% aqueous solution of sodium hydroxide and the filtrate was concentrated. The concentrate was analyzed by gas chromatography to find that a yield of 2-chloro-5-(2-aminoethyl)aminomethylpyridine was 10%.

Example 4

In a 3000 cc autoclave equipped with a magnetic stirrer, a 40% aqueous solution of methylamine (814 g), ethanol (312 g) and Raney nickel (35 g) were charged. Hydrogen gas was introduced into the autoclave to a pressure of 3 Kg/cm$^2$. While keeping a temperature at 30° C. or lower and supplying the hydrogen gas, a 58.8% solution of 2-chloro-5-trichloromethylpyridine in toluene (589 g) was added over 40 minutes. After the addition of the solution of 2-chloro-5-trichloromethylpyridine, the internal temperature was gradually raised to 40° C. At the same temperature, the hydrogen gas was supplied till the absorption of hydrogen ceased. After completion of reaction, the autoclave was cooled to room temperature, and the catalyst was filtrated off from the reaction mixture. The filtrate was analyzed by high pressure liquid chromatography to find that a yield of 2-chloro-5-methylaminomethylpyridine was 76%.

The filtrate was neutralized with a 48% aqueous solution of sodium hydroxide and concentrated. To the concentrate, toluene was added and the mixture was extracted with 35% hydrochloric acid. The extract was again neutralized with the 48% aqueous solution of sodium hydroxide and extracted with toluene. The toluene layer was concentrated to obtain 2-chloro-5-methylaminomethylpyridine in the recovery of 80%.

Example 5

In a 3000 cc autoclave equipped with a magnetic stirrer, a 70% aqueous solution of ethylamine (945 g) and Raney nickel (24 g) were charged. Hydrogen gas was introduced into the autoclave to a pressure of 3 Kg/cm$^2$. While keeping a temperature at 15° C. or lower and supplying the hydrogen gas, a 58.8% solution of 2-chloro-5-trichloromethylpyridine in toluene (825 g) was added over 3 hours. After the addition of the solution of 2-chloro-5-trichloromethylpyridine, the internal temperature was gradually raised to 35° C. At the same temperature, the hydrogen gas was supplied till the absorption of hydrogen ceased. After completion of reaction, the autoclave was cooled to room temperature, and the catalyst was filtrated off from the reaction mixture. The filtrate was analyzed by high pressure liquid chromatography to find that a yield of 2-chloro-5-ethylaminomethylpyridine was 78%.

The filtrate was concentrated and separated to an aqueous layer and an oily layer. The oily layer was extracted with 35% hydrochloric acid. The extract was neutralized with the 48% aqueous solution of sodium hydroxide and extracted with toluene. The toluene layer was concentrated to obtain 2-chloro-5-ethylaminomethylpyridine in a recovery of 75%.

Example 6

In a 500 cc autoclave equipped with a magnetic stirrer, ethylenediamine (105 g), ethanol (115 g) and Raney nickel (11.5 g) were Charged. Hydrogen gas was introduced into the autoclave to a pressure of 3 Kg/cm². While keeping a temperature at 20° C. or lower and supplying the hydrogen gas, a 58.8% solution of 2-chloro-5-trichloromethylpyridine in toluene (98 g) was added over 3 hours. After the addition of the solution of 2-chloro-5-trichloromethylpyridine, the internal temperature was gradually raised to 35° C. At the same temperature, the hydrogen gas was supplied till the absorption of hydrogen ceased. After completion of reaction, the autoclave was cooled to room temperature, and the catalyst and by-produced salt were filtrated off from the reaction mixture. The filtrate was analyzed by high pressure liquid chromatography to find that a yield of 2-chloro-5-(2-aminoethyl)aminomethylpyridine was 66%.

According to the present invention, the 2-chloro-5-aminomethylpyridine (1) can be prepared in one step process from 2-chloro-5-trichloromethylpyridine which is easily commercially available. Therefore, the 2-chloro-5-aminomethylpyridine (1) is prepared in a shorter step than the conventional process when both processes start from 3-methylpyridine.

Since the present invention process does not use skin irritative 2-chloro-5-monochloromethylpyridine, it is excellent in safety.

What is claimed is:

1. A process for preparing a 2-chloro-5-aminomethylpyridine of the formula:

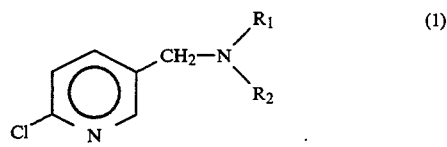

wherein $R_1$ is a hydrogen atom, an alkyl group or an aminoalkyl group, and $R_2$ is a hydrogen atom or an alkyl group, comprising reacting 2-chloro-5-trichloromethylpyridine with hydrogen and an amine of the formula:

wherein $R_1$ and $R_2$ are the same as defined above and in the presence of a hydrogenation catalyst.

2. The process according to claim 1, wherein said hydrogenation catalyst is Raney nickel.

3. The process according to claim 1, wherein the reaction is carried out while supplying hydrogen and 2-chloro-5-trichloromethylpyridine in said amine (2).

4. The process according to claim 3, wherein a reaction temperature during the supply is not more than 40° C.

5. The process according to claim 1, wherein a molar ratio of said amine to 2-chloro-5-trichloromethylpyridine is from 1:1 to 20:1.

6. The process according to claim 1, wherein an amount of said hydrogenation catalyst is 1 to 50% by weight based on the weight of 2-chloro-5-trichloromethylpyridine.

7. The process according to claim 1, wherein a pressure of hydrogen is from atmospheric pressure to 100 Kg/cm².

* * * * *